United States Patent
Podgorsky et al.

(10) Patent No.: US 12,029,435 B2
(45) Date of Patent: Jul. 9, 2024

(54) SIDE LOADING RATCHET TO STOP ARTERIAL BLEEDING DURING COMBAT TRAUMA AND THE LIKE

(71) Applicant: ARMR Systems Inc., Baltimore, MD (US)

(72) Inventors: Yegor Podgorsky, Boston, MA (US); Chibueze Joseph Ihenacho, Baltimore, MD (US); Andrew Stephens, Boston, MA (US)

(73) Assignee: ARMR Systems, Inc., Baltimore, MD (US)

(*) Notice: Subject to any disclaimer, the term of this patent is extended or adjusted under 35 U.S.C. 154(b) by 915 days.

(21) Appl. No.: 16/792,055

(22) Filed: Feb. 14, 2020

(65) Prior Publication Data
US 2020/0261099 A1  Aug. 20, 2020

Related U.S. Application Data

(60) Provisional application No. 62/805,657, filed on Feb. 14, 2019.

(51) Int. Cl.
*A61B 17/132* (2006.01)
*A61B 17/00* (2006.01)

(52) U.S. Cl.
CPC ... *A61B 17/1325* (2013.01); *A61B 2017/00407* (2013.01)

(58) Field of Classification Search
CPC ...... A61B 17/1325; A61B 2017/00407; A61B 17/1322; A61B 17/132; A61H 11/00; A61H 2201/164; A61H 2205/081; A61H 2205/086; A61H 2201/0134; A61H 2011/005; A61H 2201/0107; A61H 2201/0176

See application file for complete search history.

(56) References Cited

U.S. PATENT DOCUMENTS

2010/0137900 A1 * 6/2010 Chao ............... A61B 17/1327
                                                606/203
2019/0274693 A1 * 9/2019 Carson ............ A61B 17/1327

* cited by examiner

*Primary Examiner* — Sarah W Aleman
*Assistant Examiner* — Mikail A Mannan
(74) *Attorney, Agent, or Firm* — Foley Hoag LLP; John Lanza

(57) ABSTRACT

Described embodiments provide systems and methods for a tourniquet system compression device. The compression device includes a spooling mechanism, a ratchet release, a safety release, and a profile surface. The spooling mechanism includes a first side loading configured to receive a first tourniquet strap, and a second side loading slot configured to receive a second tourniquet strap. The ratchet release disengages a ratchet gear from a pawl. The safety release prevents the ratchet gear from disengaging with the pawl when the safety release is active. The profile surface generates a pressure profile against a subject. The compression device includes a fixed end of webbing. The compression device is coupled to the webbing. The spooling mechanism is configured to gather the webbing. The compression device includes a preset pressure profile. The compression device includes a fixed end fitting. The compression device is configured for side entry loading of the webbing.

12 Claims, 15 Drawing Sheets

714

SIDE LOADING RATCHET TO STOP ARTERIAL BLEEDING DURING COMBAT TRAUMA AND THE LIKE

CROSS-REFERENCE TO RELATED PATENT APPLICATIONS

This application claims priority to U.S. Provisional Patent Application No. 62/805,657 filed on Feb. 14, 2019 and titled "INTEGRATED HEMORRHAGE CONTROL DEVICE," which is herein incorporated by reference in its entirety.

FIELD OF THE INVENTION

The present invention relates to a novel way to tighten/ increase tension in straps via a side loading ratcheting mechanism.

BACKGROUND

A tourniquet can be used to stop or reduce bleeding that can occur as the result of an injury. The tourniquet can be used to control venous and arterial circulation to the site of the injury. The tourniquet can control the blood flow by applying pressure to the tissue underlying the tourniquet. The applied pressure can occlude the vessels, and prevent or reduce flow there through.

SUMMARY

Junctional tourniquets are devices that attempt to treat arterial hemorrhage through the use of direct pressure on the arteries at the junctional areas of the extremities. Webbing straps can be used to constrict or compress the body to prevent blood flow to a portion of an extremity for a period of time. The tourniquet system applies direct pressure to an artery by tightening or increasing tension in webbing straps wrapped around the subject. The tourniquet system includes a first side loading ratchet to spool the webbing. The tightening combined with the system's pressure profile provides pressure to the artery and limit blood loss. In the event of a traumatic injury, the tourniquet can be used to stop bleeding long enough for the injured person to get access to proper medical attention.

According to one aspect, a tourniquet system is disclosed. The tourniquet system includes a compression device. The compression device includes a spooling mechanism, a ratchet release, a safety release, and a profile surface. The spooling mechanism includes a first side loading configured to receive a first tourniquet strap, and a second side loading slot configured to receive a second tourniquet strap. The ratchet release disengages a ratchet gear from a pawl. The safety release prevents the ratchet gear from disengaging with the pawl when the safety release is active. The profile surface generates a pressure profile against a subject.

In some implementations, the compression device includes a fixed end of webbing. In certain implementations, the compression device is coupled to the webbing. In certain implementations, the spooling mechanism is configured to gather the webbing. In certain implementations, the compression device includes a preset pressure profile.

In some implementations, the compression device includes a fixed end fitting. In some implementations, the compression device is configured for side entry loading of the webbing. In some implementations, the webbing is configured to press into the subject. In some implementations, the ratchet release includes a button to actuate the ratchet release. In some implementations, the button moves the ratchet gear from the pawl.

In another aspect, a tourniquet system includes a compression device. The compression device includes a spooling mechanism, a ratchet release, a safety release, and a profile surface. The spooling mechanism includes a side loading slot configured to receive a tourniquet strap. The compression device includes a ratchet release disengaging a pawl from a ratchet gear. The safety release prevents the pawl from disengaging with the ratchet gear when the safety release is active. The profile surface to generate a pressure profile against a subject.

In another aspect, a method for controlling a hemorrhage is described. The method includes providing a hemorrhage control device including a compression device. A webbing loads into a first loading slot of the compression device. The webbing is tightened using the compression device to apply pressure to a fixed end arterial area of a body. A ratchet release of the compression device activates to enable blood flow to a limb of a subject.

In some implementations, the compression device provides a spooling mechanism. The spooling mechanism includes a first side loading slot configured to receive the webbing, and a second side loading slot configured to receive the webbing. The compression device includes a safety release to prevent a pawl from disengaging with a ratchet gear when the safety release is active. The compression device includes a profile surface to generate a pressure profile against a location. The ratchet release disengages the ratchet gear from the pawl. The webbing loads into the second loading slot of the compression device. In certain implementations, the webbing loads into the second side loading slot of the compression device. In some implementations, a button disengages the ratchet gear from the pawl. In some implementations, tightening the webbing includes lifting up and down on a ratchet handle to apply pressure by the profile surface to a fixed end arterial area of a body.

In some implementations, the compression device includes a spooling mechanism. The spooling mechanism includes the first loading slot configured to receive a tourniquet strap. The compression device includes a safety release to prevent a pawl from disengaging with a ratchet gear when the safety release is active. The compression device includes a profile surface to generate a pressure profile against a location. The ratchet release disengages the pawl from the ratchet gear.

In some implementations, the webbing tightens around a junctional area. In some implementations, a handle engages an internal ratcheting system. In some implementations, a barrel twists the webbing.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

In some implementations, the systems and methods described herein are configured to simultaneously apply a compressive pressure to tissue, such as that at a junctional area, and a constrictive pressure around the tissue to control venous and arterial circulation. As an overview, the system can include a harness that is worn by the wearer prior to an injury. A compression device can be coupled to the harness. As a user rotates the handle of the compression device, the harness spools around the compression device. The spooling of the harness constricts the harness around the target tissue and simultaneously drives the compression device into the tissue.

Figure 1:
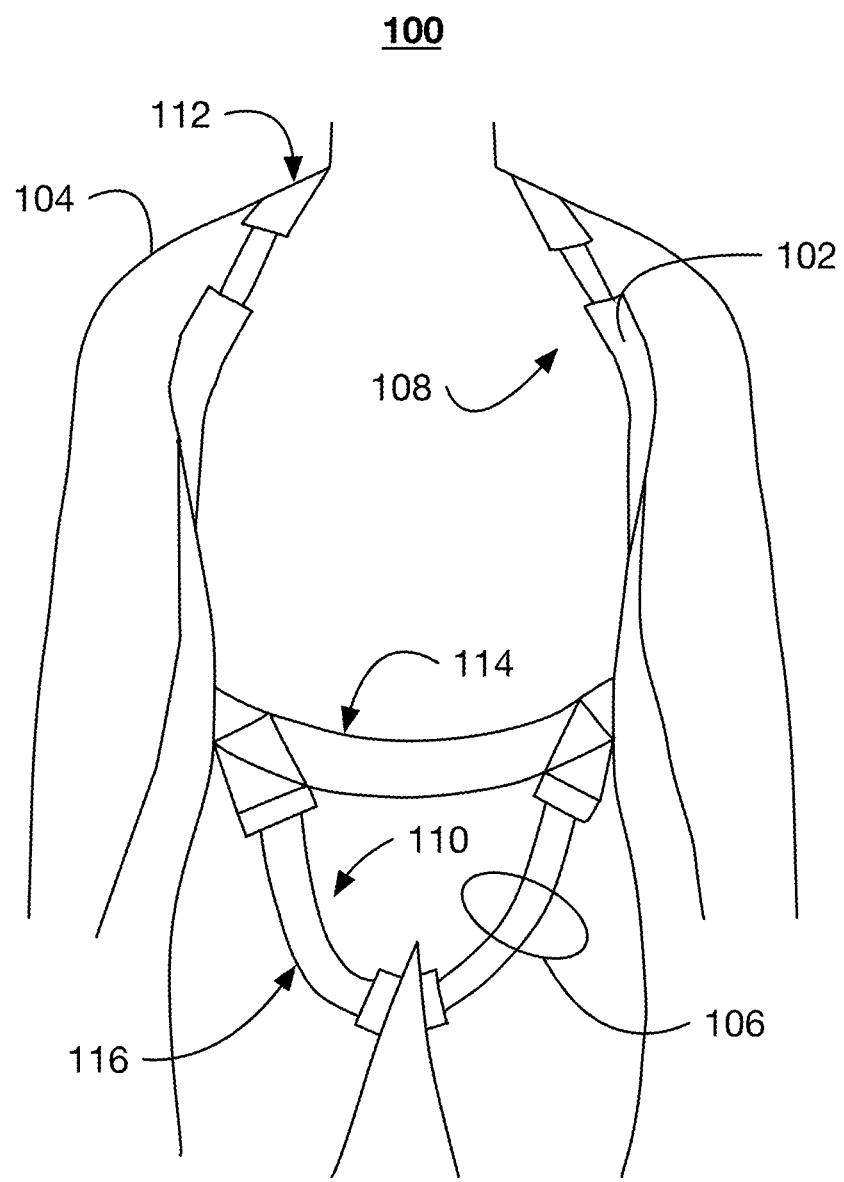
FIG. 1 illustrates an example system for hemorrhage control.

Referring now to FIG. 1, an example system 100 for hemorrhage control is illustrated. The system 100 includes a harness 102 that is worn by a wearer 104. The harness 102 is worn by the wearer 104 around at least one upper junctional area 108 and at least one lower junctional area 110. The system 100 also includes at least one compression device 106 that is reversibly coupled to the harness 102. As illustrated in FIG. 1, the compression device 106 is coupled to the harness 102 at one of the wearer's lower junctional areas 110. As further described below, the compression device 106 includes a compression puck that can be used to apply pressure to the wearer's upper junctional area 108 or lower junctional area 110. A plurality of compression devices 106 can be coupled to the harness 102 at any one time. For example, a plurality of compression device 106 can be applied over a single junctional area, one compression device 106 can be applied at a plurality of junctional areas, or a plurality compression device 106 can be applied at a plurality of junctional areas. The compression device 106 also includes a handle that is configured to constrict the harness 102 around the wearer's upper junctional area 108 or lower junctional area 110 when rotated. The constriction of the harness can cause the depression of the compression puck into the wearer's upper junctional area 108 or lower junctional area 110. The compression device 106 can also include a ratchet mechanism that enables the handle to rotate in substantially only one direction and maintains the constriction of the harness 102 around the wearer's upper junctional area 108 or lower junctional area 110.

Still referring to FIG. 1, the system 100 includes the harness 102. As an overview, the harness 102 is worn by the wearer 104 prior to use of the system 100. For example, the harness 102 may be worn by a soldier as part of the everyday combat dress. In this example, if the solider is injured and requires a tourniquet, the compression device 106 can be coupled to the harness 102 and used to apply pressure to the soldier's wounds or to injured blood vessels. Wearing the harness 102 prior to the need for a tourniquet can reduce the total amount of time required to stop (or reduce) blood flow to an injury because the soldier is already wearing the harness 102 and a constriction mechanism (e.g., a strap or cuff) does not also need to be applied to the soldier. In some implementations, all or part of the harness 102 can be applied to wearer after the injury. For example, the harness be worn around the waist and shoulders of a wearer and the leg straps of the device may be deployed after the injury. The harness 102 can be worn and encircle (partially or totally) at least one upper junctional area 108 and at least one lower junctional area 110. In some implementations, the harness 102 may only encircle one or more upper junctional areas 108 or one or more lower junctional areas 110. A junctional area of the wearer 104 includes the areas of the wearer's body near where the trunk of the wearer 104 joints the appendages, such as the arms and legs. The upper junctional areas 108 can include the areas of the wearer's body where the trunk meets the arms, and the lower junctional areas 110 can include the areas of the wearer's body where the trunk meets the legs. Major arteries and veins can pass through the junctional areas of the wearer 104. For example, the femoral, iliac, and aortic arteries can pass through the lower junctional area 110, and the axillary and subclavian arteries can pass through the upper junctional area 108. In some implementations, the harness 102 is configured to cross other major and minor arteries and veins. As illustrated in FIG. 1, the harness 102 includes an over-the-shoulder component 112 that encircles the wearer's two upper junctional areas 108. The harness 102 also includes a waist component 114 with two leg straps 116 that encircle each of the wearer's lower junctional areas 110.

Still referring to FIG. 1, the harness 102 can be manufactured from a nylon webbing, polypropylene, or a similar fabric. In some implementations, the harness 102 includes pouches constructed from a rip-stop fabric, such as rip-stop nylon fabric. The pouches can be used to store the leg straps 116 when not in use. The various components of the harness 102 can be sewn together with treads containing, nylon, cotton, polyester, viscose, rayon, or a combination thereof. In some implementations, the harness 102 is constructed to meet military specifications. The straps of the harness 102 can be between about 1 inch and about 3 inches, between about 1 inch and about 2 inches, or between about 1 inch and about 1.5 inches. In some implementations, different portions of the harness 102 are constructed with different sized straps. For example, portions of the harness 102 that interface with the compression device 106 can be manufactured from 1 inch wide straps while the portions of the compression device 106 not intended to interface with the compression device 106 can be manufactured from 1.5 inch wide straps. In some implementations, the harness 102 is sized according to the size of the wearer 104. In other implementations, the harness 102 can be manufactured in specific sizes (e.g., small, medium, and large). The harness 102 can include one or more buckles and fasteners, such as a snap-fit buckle, that enables to wearer 104 to adjust the fit of the harness 102 and that can also facilitate the wearer 104 in putting on the harness 102. For example, rather than stepping through the loops created by each of the leg straps 116, the leg straps 116 can include snap-fit buckles that enable to wearer 104 to pull the leg straps 116 forward and under the leg from their attachment point on the side or back of the waste component 114 and connect the leg straps 116 to the front of the waist component 114.

Figure 2:
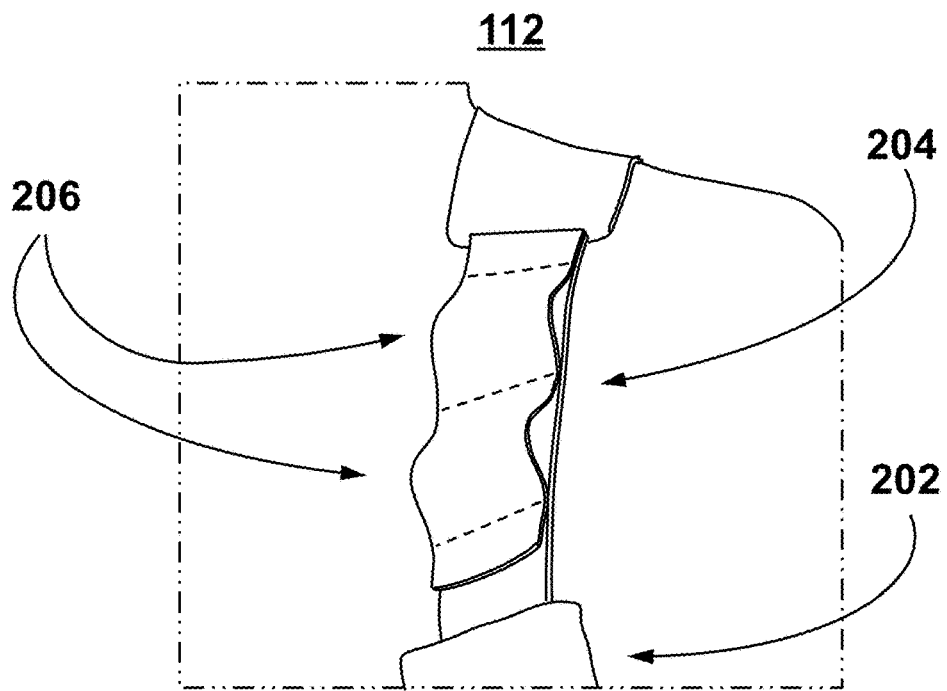
FIGS. 2-4 illustrate enlarged views of an example harness for use in the system illustrated in FIG. 1.
Figure 3:
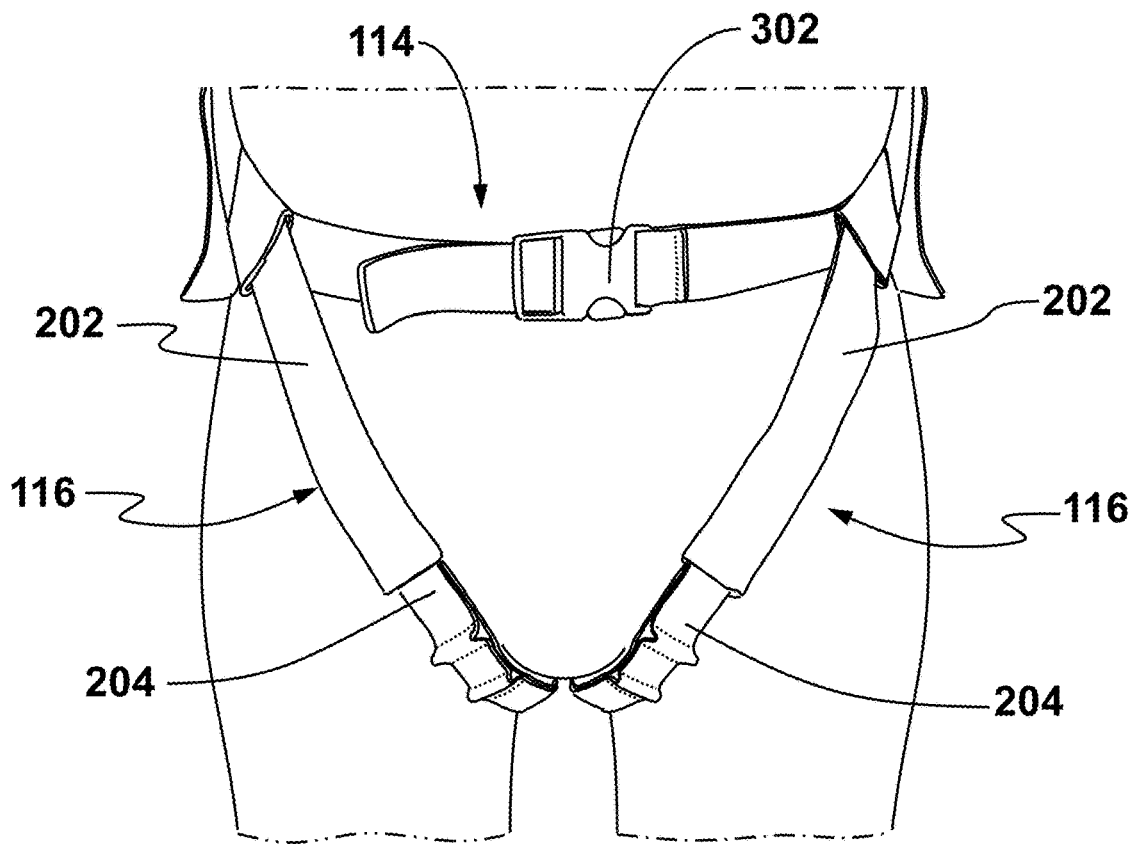
Figure 4:
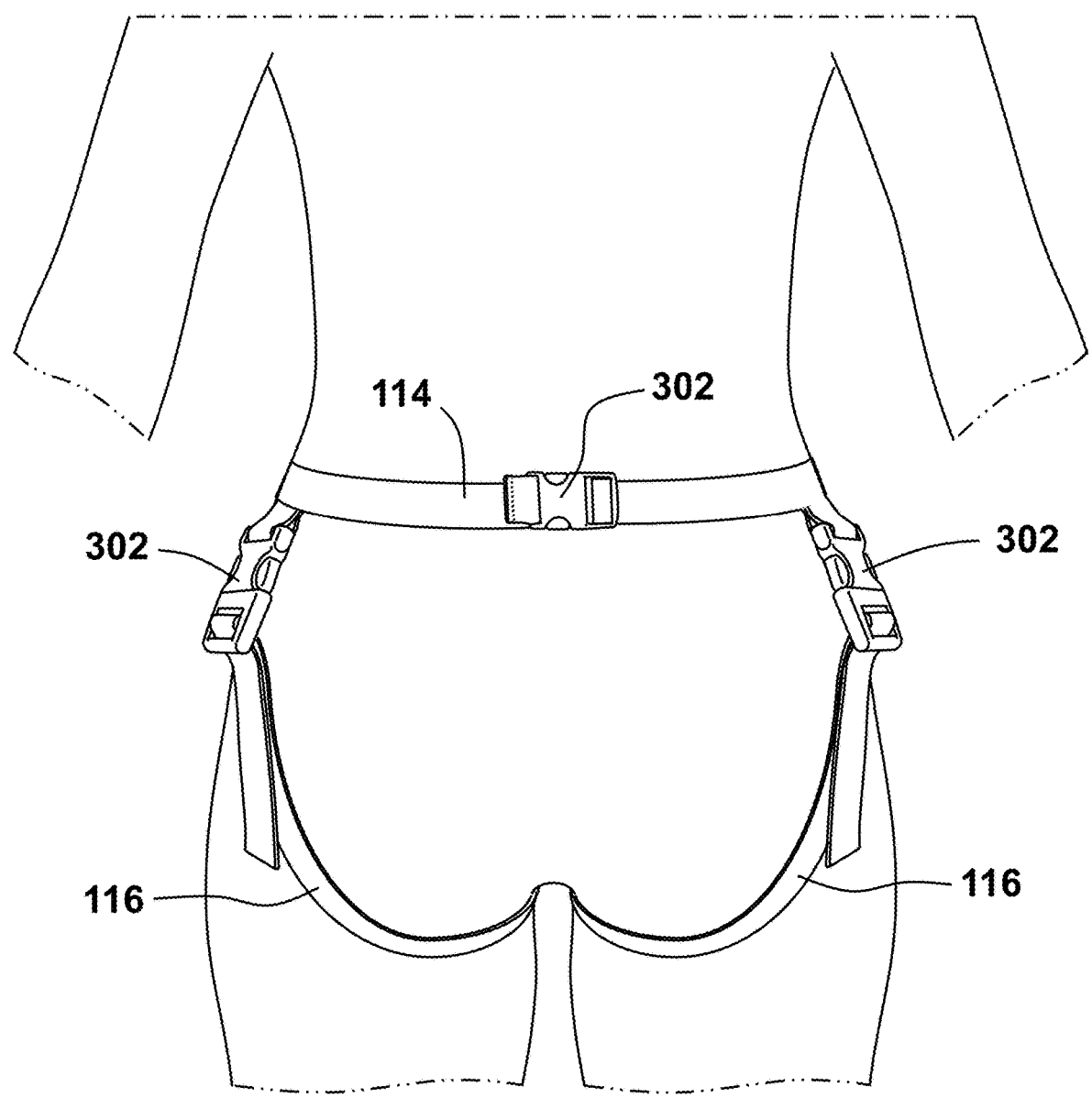

Still referring to FIG. 1, the harness 102 is described further in relation to FIGS. 2-4. Referring now to FIG. 2, illustrated is an enlarged view of the over-the-shoulder component 112 of the harness 102. As described above, in some implementations, the harness 102 can include different widths of strap for the portions of the harness 102 that interact with the compression device 106. FIG. 2 illustrates that the harness 102 includes a wider portion 202 and a narrow portion 204. The narrow portion 204 is configured to interact (e.g., reversibly couple) with the compression device 106. The narrow portion 204 (or other portions of the harness 102) can include modular lightweight load-carrying equipment (MOLLE) loops 206 to facilitate the coupling of the compression device 106 with the harness 102.

Referring now to FIG. 3, illustrated is an enlarged view of the lower, front portion of the harness 102 when worn by the wearer 104. The lower portion of the harness 102 includes the waist component 114 with two leg straps 116 that wrap around each of the lower junctional areas 110. The waist component 114 includes a snap-fit buckle 302 that enables the wearer 104 to secure and tighten the waist component 114 about the wearer's abdomen. Each of the leg straps 116 can include a wider portion 202 and a narrow portion 204.

Referring now to FIG. 4, illustrated is an enlarged view of the lower, back portion of the harness 102 when worn by the wearer 104. The back of the waist component 114 can include a buckle 302. In some implementations, the harness 102 can include a plurality of buckles that enable the harness 102 to be quickly removed from the wearer 104. For example, the plurality of buckles can facilitate medical professionals or others in quickly removing the harness 102 during emergency or other situations.

Still referring to FIG. 4, illustrated are the buckles 302 can be included in the leg straps 116 for easy deployment of the leg straps 116. In some implementations, the waist component 114 includes one or more pouches to store the leg straps 116 when the leg straps 116 are not wrapped around the lower junctional areas 110 of the wearer 104.

Figure 5:
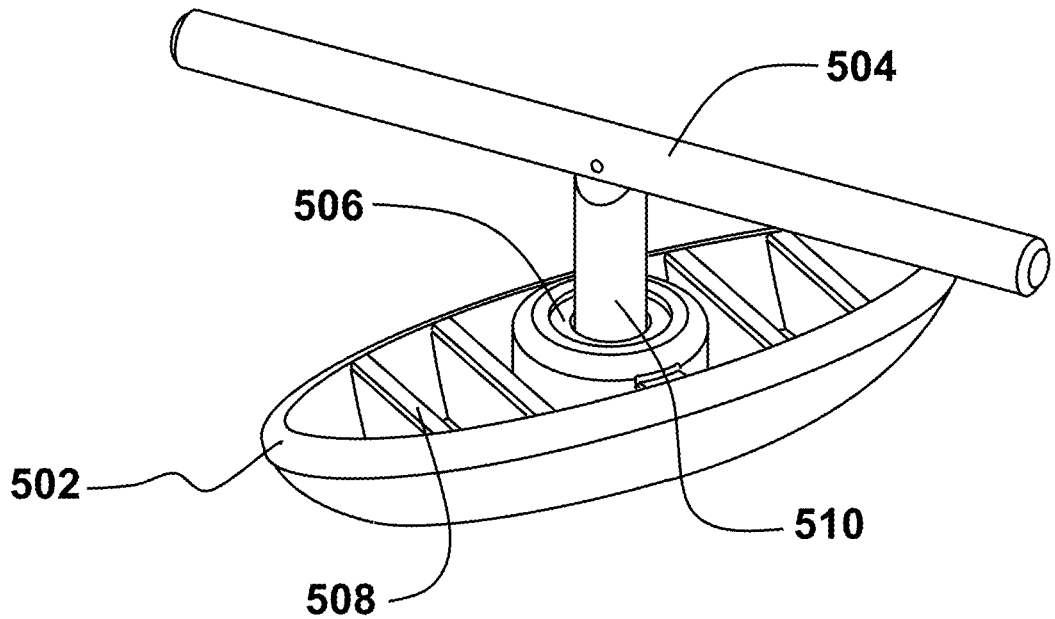
FIG. 5 illustrates a perspective view of an example compression device for use in the system illustrated in FIG. 1.

Referring now to FIG. 5, illustrated is the compression device 106 including a compression puck 502 (also referred to as a puck 502) that is configured to apply pressure to a junctional area of the wearer 104. The compression device 106 also includes a handle 504. The handle 504 is coupled to the puck 502 with a ratchet mechanism 506.

Still referring to FIG. 5, the puck 502 of the compression device 106 can be oval shaped. The puck 502 can taper toward the base of the puck 502. In other implementations, the puck 502 is circular, square, rectangular, or any other shape that can distribute pressure to the arteries to substantially constrict the flow of blood through the arteries. The corners of the puck 502 can be rounded to reduce the chance of injuring the wearer 104 when the puck 502 is compressed into the junctional area of the wearer 104. The puck 502 includes a plurality of support structures 508, such as ribs, that provide rigidity to the puck 502. In other implementations, the puck 502 can be a solid block of material. The puck 502 can be manufactured from acrylonitrile butadiene styrene (ABS) plastic, aluminum, stainless steel, rubber, glass filled nylon, carbon fiber, polyether ether ketone (PEEK), nylon, 3-D printed materials, polyethylene terephthalate (PET). The puck 502 can be machined from a bulk material, 3D printed, or injection molded. In some implementations, the bottom of the puck 502 (e.g., the surface of the puck 502 in contact with the wearer 104) is textured so that the puck 502 stays in place when pressed into the wearer 104. For example, the bottom of the puck 502 can include knurling or a soft textured pad that aids in the grip of the puck 502. In some implementations, the length of the puck 502 is between about 2 inches and about 8 inches, between about 3 inches and about 7 inches, or between about 4 inches and about 6 inches. In some implementations, the width of the puck 502 can be between about 1 inch and about 8 inches, between about 2 inches and about 7 inches, or between about 3 inches and about 6 inches. For example, an oval puck may be about 4.25 inches long by about 1.5 inches wide. In some implementations, the puck 502 is between about 0.5 inches and about 3 inches, between about 0.5 inches and about 2 inches, or between about 0.5 inches and about 1 in tall.

Still referring to FIG. 5, the compression device 106 can also include a ratchet mechanism 506. The ratchet mechanism 506 can be configured to enable the handle 504 to rotate in substantially only one direction. For example, as a user rotates the handle 504 clockwise, the ratchet mechanism 506 can prevent the handle 504 from rotating counterclockwise when the user releases the handle 504. The ratchet mechanism 506 can enable the pressure applied by the puck 502 and the constrictive pressure applied by the harness 102 to be maintained without the need for a user to hold the handle 504 in place. In some implementations, the ratchet mechanism 506 includes a drawn-cup needle roller bearing, ball roller bearing, threaded mechanisms (e.g., screws), ratchets with a catching teeth mechanism. The compression device 106 can also include a securing latch, pin, or strap that can be coupled to the handle 504 (or other component of the compression device 106) to prevent the handle 504 from unwinding after a portion of the harness 102 is wound around the handle 504. In some implementations, the puck 502 can include a locking mechanism in place of, or in addition to, the ratchet mechanism 506. For example, the user may be able to rotate the handle 504 clockwise and then lock the handle 504 in place with a pin that prevents the handle from rotating counterclockwise.

Still referring to FIG. 5, the compression device 106 can also include the handle 504. The handle 504 (and shaft 510 thereof) can be manufactured from stainless steel, aluminum, titanium, rubber, glass filled nylon, carbon fiber, polyether ether ketone (PEEK), nylon, 3-D printed materials, polyethylene terephthalate (PET), or a combination thereof. In some implementations, the length of the handle 504 is between about 3 inches and about 8 inches, between about 4 inches and about 7 inches, or between about 5 inches and about 6 inches long. The diameter of the handle 504 can be between about 0.25 inches and about 1 inch, between about 0.25 inches and about 0.75 inches, or between about 0.30 inches and about 0.50 inches wide. In some implementations, the height of the shaft 510 of the handle 504 is between about 1.0 inches and about 4 inches, between about 1.5 inches and about 3 inches, or between about 1.5 inches and about 2 inches tall. In some implementations, the shaft 510 and handle 504 are configured to reversibly mate with one another. For example, the top of the shaft 510 may be keyed to mate with a hole in the bottom of the handle 504. This may enable the handle 504 be removed from the compression device 106 for storage, and then coupled with the shaft 510 just prior to use.

Figure 6:
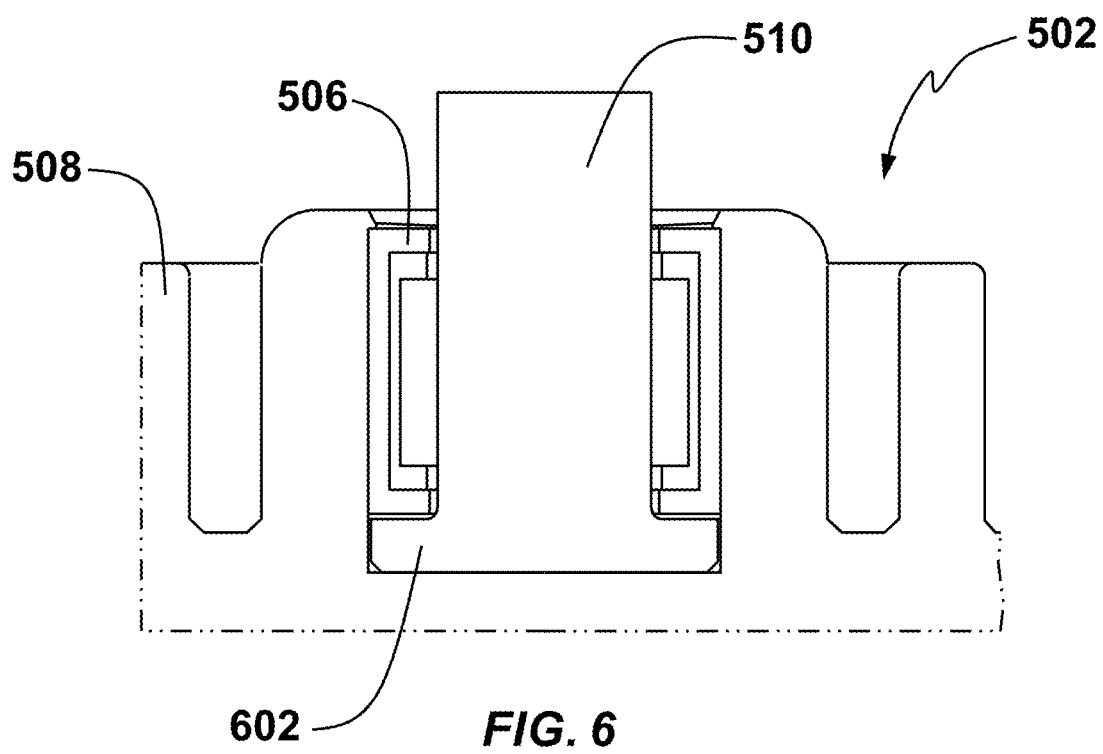
FIG. 6 illustrates a cross sectional view of the ratchet mechanism of the example compression device illustrated in FIG. 5.
Figure 7A:
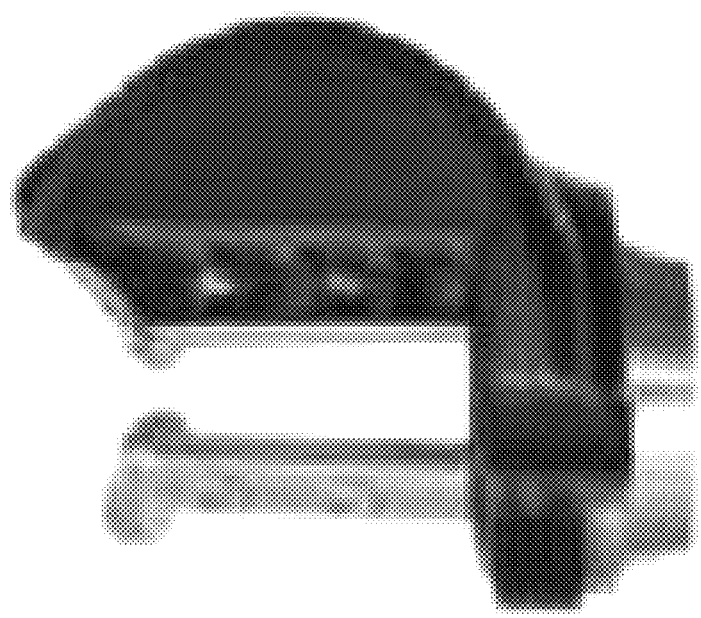
FIGS. 7A-7F are various views of an alternate implementation of the compression device.
Figure 7B:
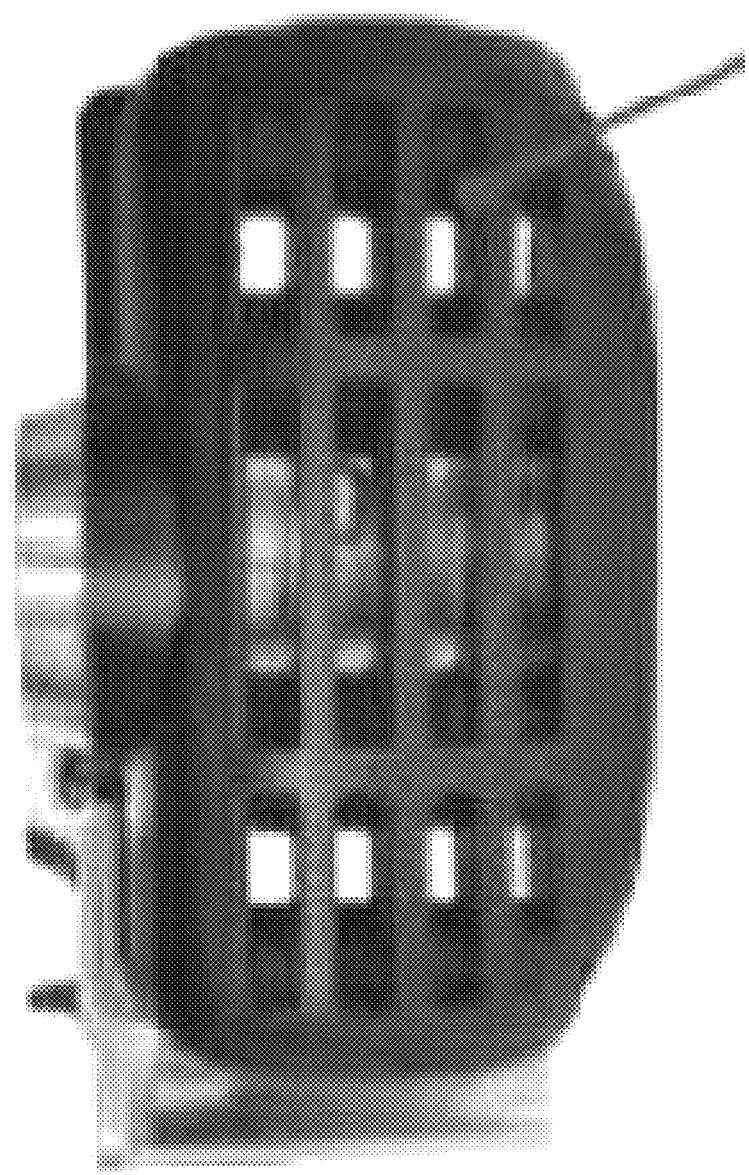
Figure 7C:
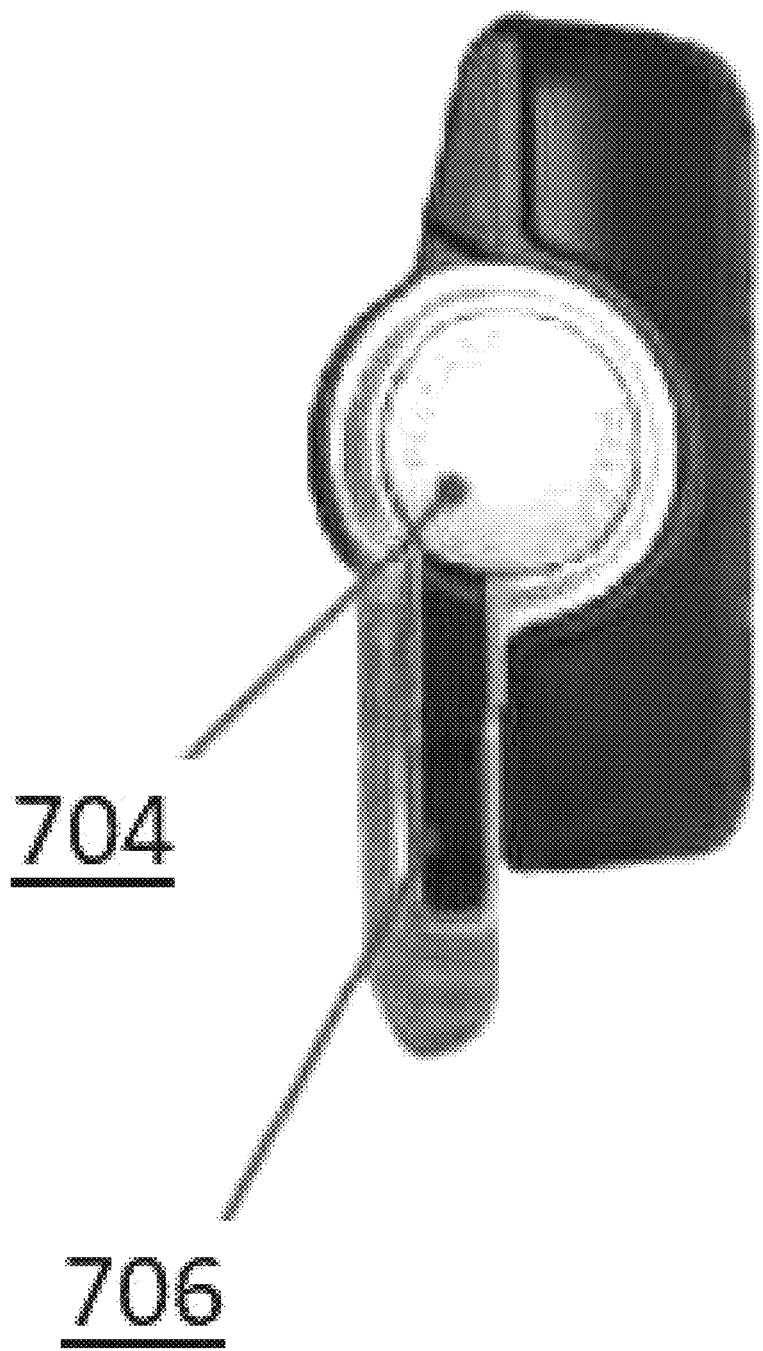
Figure 7D:
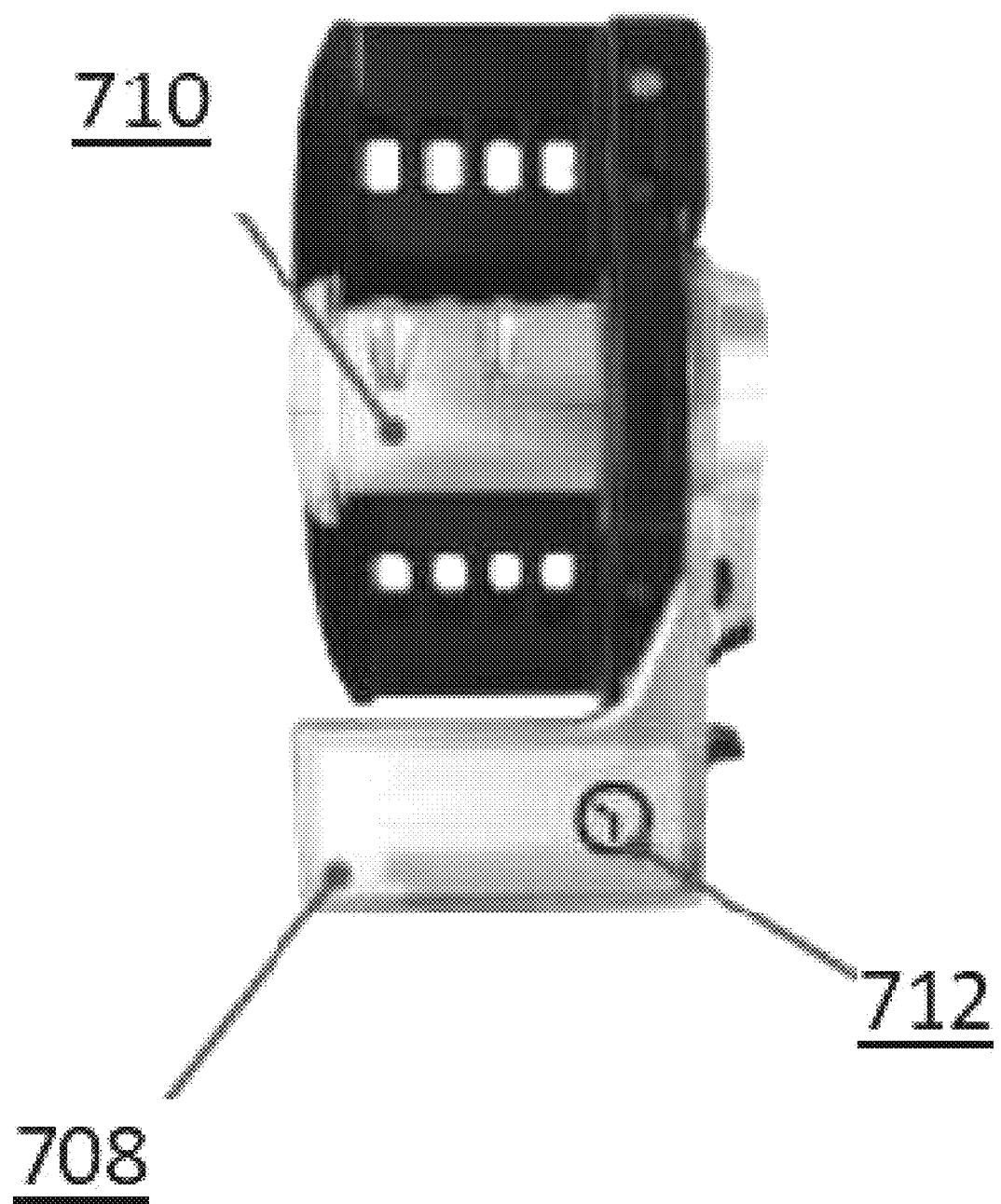
Figure 7E:
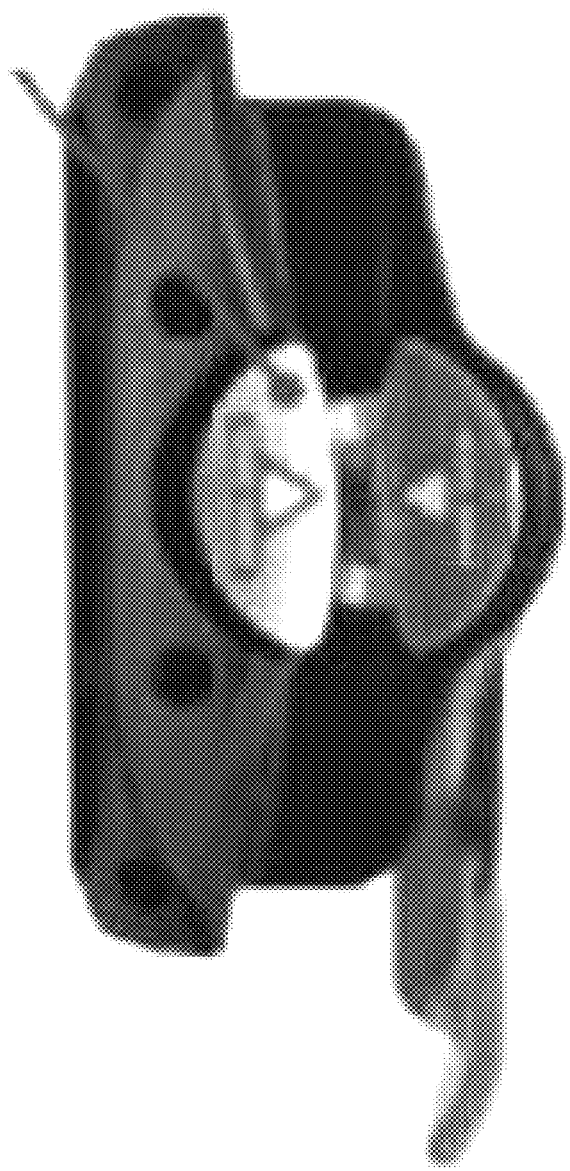
Figure 7F:
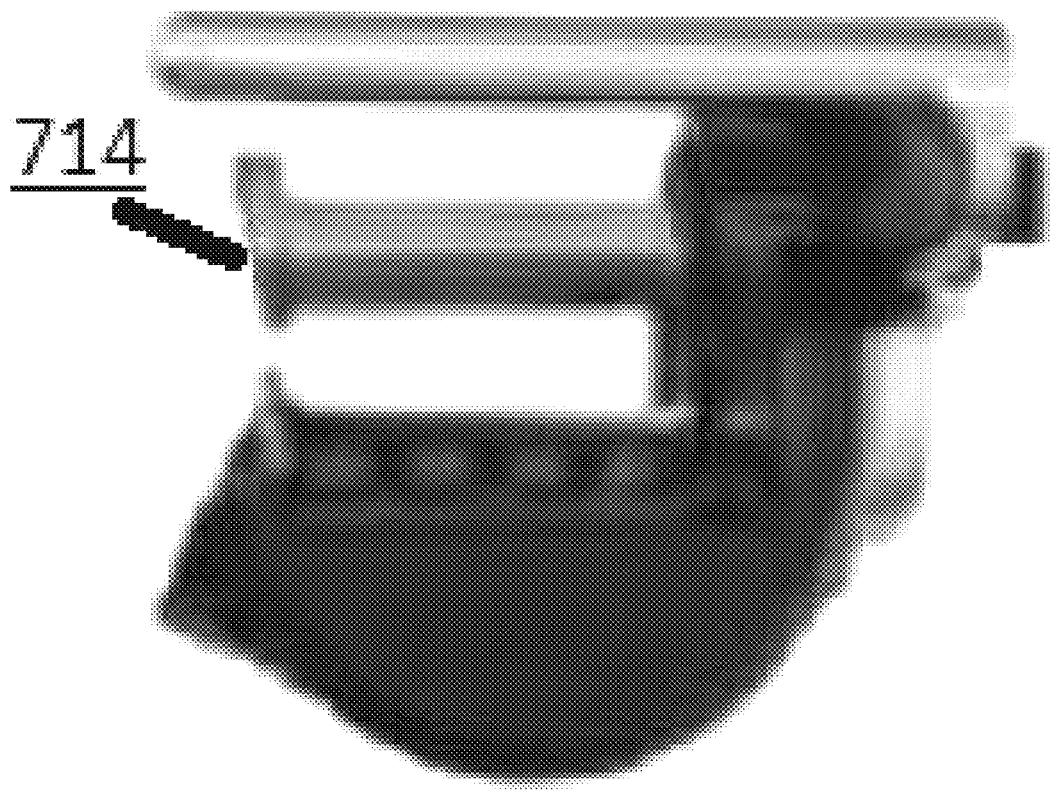

Referring now to FIG. 6, illustrated is a cross sectional view of the ratchet mechanism 506. The shaft 510 can include a lip 602 that prevents the shaft 510 from being removed from the compression device 106. In some implementations, a thin film of Teflon can rest between the bottom of the lip 602 and the puck 502 to reduce the friction between the shaft 510 and the puck 502 when the shaft 510 rotates. The ratchet mechanism 506, shaft 510, lip 602, or any combination thereof can be greased to reduce friction.

FIGS. 7-11 illustrate alternate embodiments of the compression device. Referring now to FIGS. 7A-7F, illustrated are various views of an implementation of the compression device 106. Referring now to FIG. 7A, illustrated is the back view of the compression device 106. Referring now to FIG. 7B, illustrated is the bottom view of the compression device 106. The bottom of the compression device 106 can include a profiled surface 702 that generates a pressure profile designed to put force against the body and apply pressure to the area. Referring now to FIG. 7C, illustrated is the left view of the compression device 106. The compression device 106 can include a release system 704. The release system 704 can include button that can be pressed inwards to move the gear away from the pawl. The release system can enable a user to release tension in the webbing. The compression device 106 can function by two pawls operating against a ratchet gear. To operate the ratchet gear, the user lifts up and down on the handle. To release, the user presses the button which moves the gear away from the pawls, enabling the spooling mechanism to rotate freely. The compression device can include a safety release 706. The safety release 706 can prevent accidental release of the system. Referring now to FIG. 7D, illustrated is the top view of the compression device 106. The compression device can include a ratchet handle 708. A user can use the ratchet handle 708 to engage with and activate the internal ratcheting system. The compression device can include a spooling mechanism 710. The spooling mechanism 710 can include a barrel that twists the webbing. The compression device can include a surface 712 where a user can write or place information, such as the time that the tourniquet was applied. Referring now to FIG. 7E, illustrated is the right view of the compression device 106. The compression device can include a side insertion slot 714 where the webbing is inserted into the barrel of the spooling mechanism. The side insertion slot 714 can be slanted as to provide easier sideways strap insertion. Referring now to FIG. 7F, illustrated is the front view of the compression device 106. The side insertion slot 714 provides easier sideways strap insertion.

Figure 8:
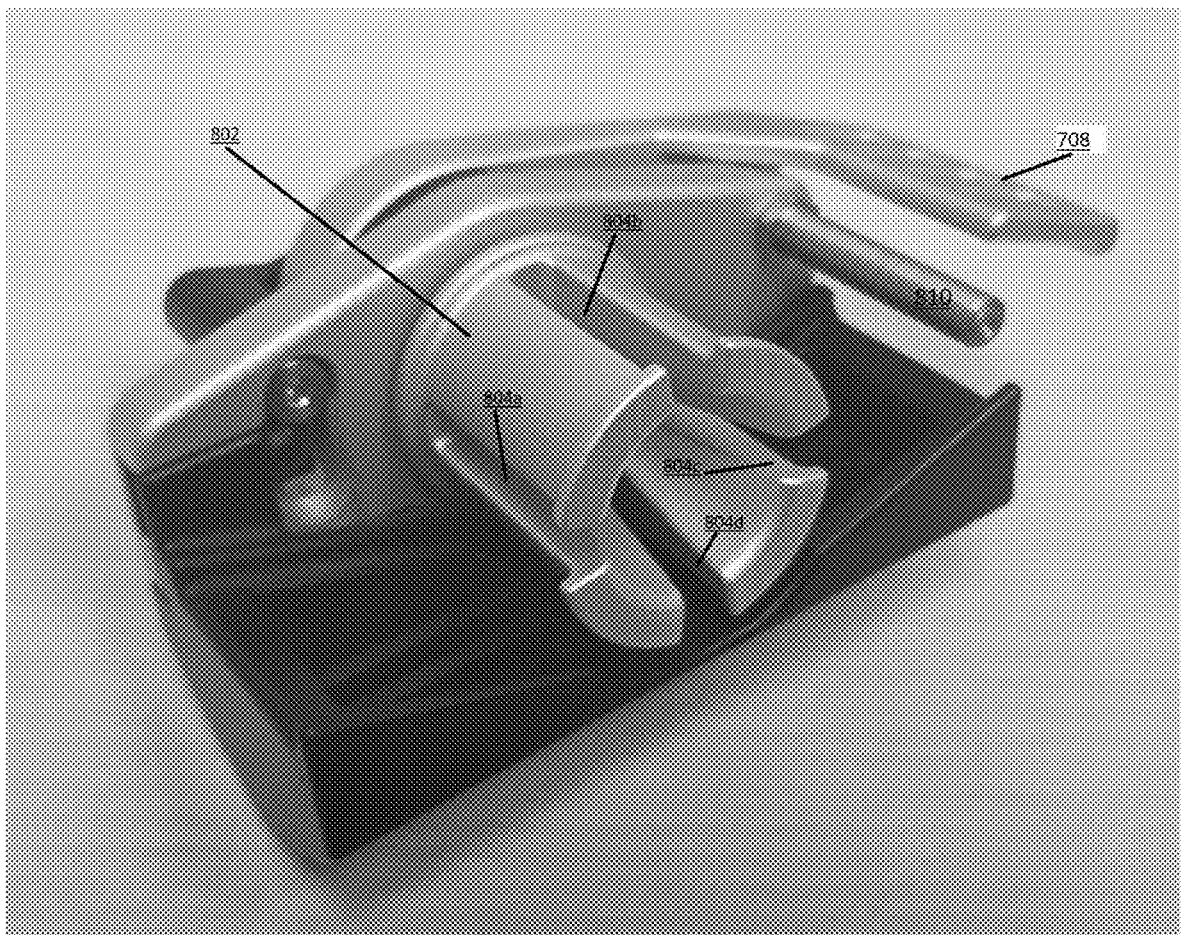
FIGS. 8 and 9 illustrates views of different example spooling mechanisms.
Figure 9:
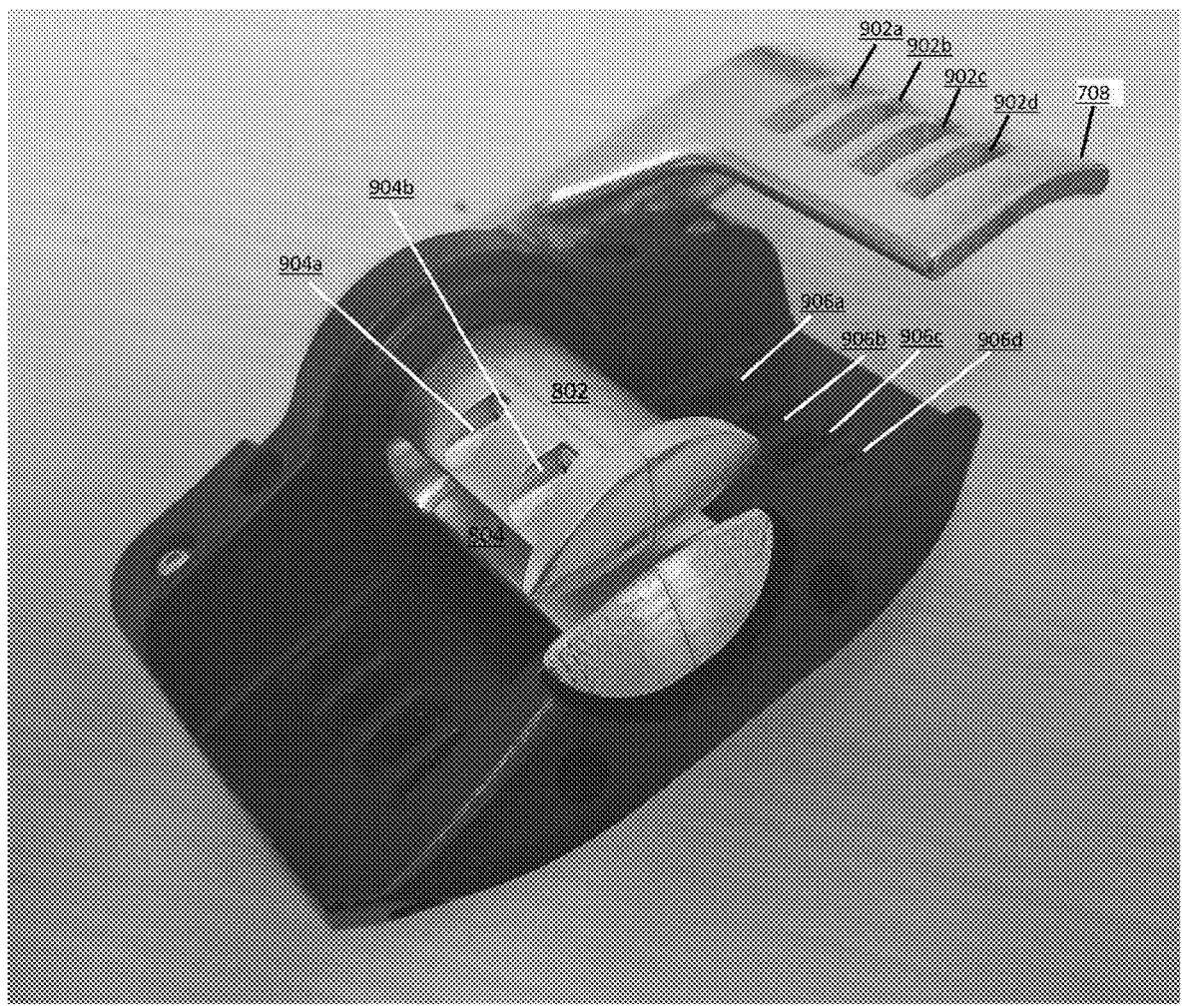

FIGS. 8 and 9 illustrate example barrels for the compression device 106. Referring now to FIG. 8, illustrated is the compression device 106*a*. The release system can be configured as a lever. In an alternate implementation, the release system is configured by a button. The release system can move or disengage the pawls away from the central ratchet gear. In some implementations, the barrel 802 has a cylindrical shape. A barrel 802 can include four slots 804*a*-804*d* (generally referred to as slot 804) for the placement of the webbing. In some implementations, the barrel includes a slot 804 every 90 degrees. In some implementations, the barrel includes a slot 804 every 45 degrees. The barrel can include an additional slot 804 as long as the structural integrity of the barrel is maintained. The additional slot would be for the insertion of the webbing strap. A metal bar 810 adds strap pressure and stability. In some implementations, the metal bar 810 adds webbing pressure and stability. In some implementations, the metal bar 810 makes the webbing stay against the body of the pressing device.

Referring now to FIG. 9, illustrated is the compression device 106*b*. The compression device 106*b* includes a single slot for the placement of the webbing. A lever operates the release system. The barrel 802 is a cylindrical shape. The slot 804 is available for the placement of the webbing. The ratchet handle 708 includes slits 902*a*-902*d* (generally referred to as slit 902). The slit 902 provides grip for operating the ratchet handle 708. In some implementations, each slit 902 of the slits 902*a*-902*d* are equidistant. In some implementations, the ratchet handle 708 only includes slit 902*a*. In some implementations, the ratchet handle 708 only includes slit 902*a* and 902*b*. In some implementations, the ratchet handle 708 only includes slit 902*a*, 902*b*, and 902*c*.

Still referring to FIG. 9, in some implementations, the compression device 106*b* includes barrel slits 904*a*-904*b* (generally referred to as barrel slit 904). In some implementations, the barrel slit 904 provides aerodynamic support for inserting the webbing. In some implementations, the barrel slit 904 provides grip on the webbing. In some implementations, each barrel slit 904 of the barrel slits 904*a*-9064 are equidistant. In some implementations, the compression device 106*b* only includes barrel slit 904*a*.

Still referring to FIG. 9, in some implementations, the compression device 106*b* includes profile surface slits 906*a*-906*d* (generally referred to as profile surface slit 906). In some implementations, the profile surface slit 906 provides aerodynamic support for operating the ratchet handle. In some implementations, the profile surface slit 906 provides grip on the subject. In some implementations, each profile surface slit 906 of the profile surface slits 906*a*-906*d* are equidistant. In some implementations, the compression device 106*b* only includes profile surface slit 906*a*. In some implementations, the compression device 106*b* only includes profile surface slit 906*a* and profile surface slit 906*b*. In some implementations, the compression device 106*b* only includes profile surface slit 906*a*, profile surface slit 906*b*, and profile surface slit 906*c*.

Figure 10:
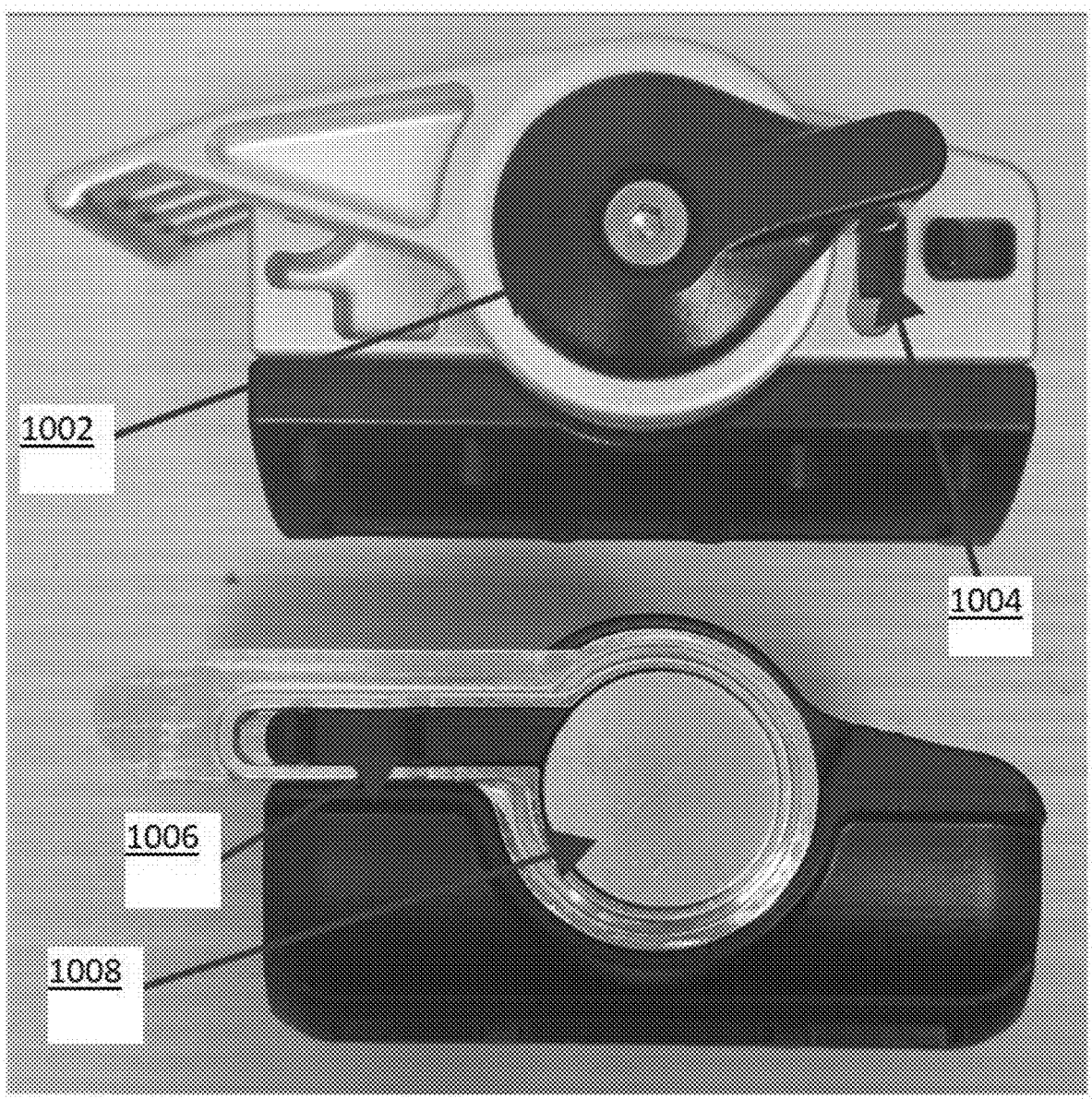
FIG. 10 illustrates a side view of the compression device.

Referring now to FIG. 10, illustrated is a side view comparison of the compression device 106*a* and compression device 106*b*. In particular, there is a difference between the release system 1002 of the compression device 106*a* illustrated in FIG. 8 and the release system 1008 of the compression device 106*b* illustrated in FIG. 9. The release system 1004 can function via moving or disengaging the internal ratchet gear away from the pawls. The release system 1008 can function by moving the pawl away from the gear. The release system 1002 is a lever whereas the release system 1008 is a button. The compression device 106*a* includes safety release 1004 and compression device 106*b* includes safety release 1006. The safety releases can prevent the release mechanism from moving.

Figure 11:
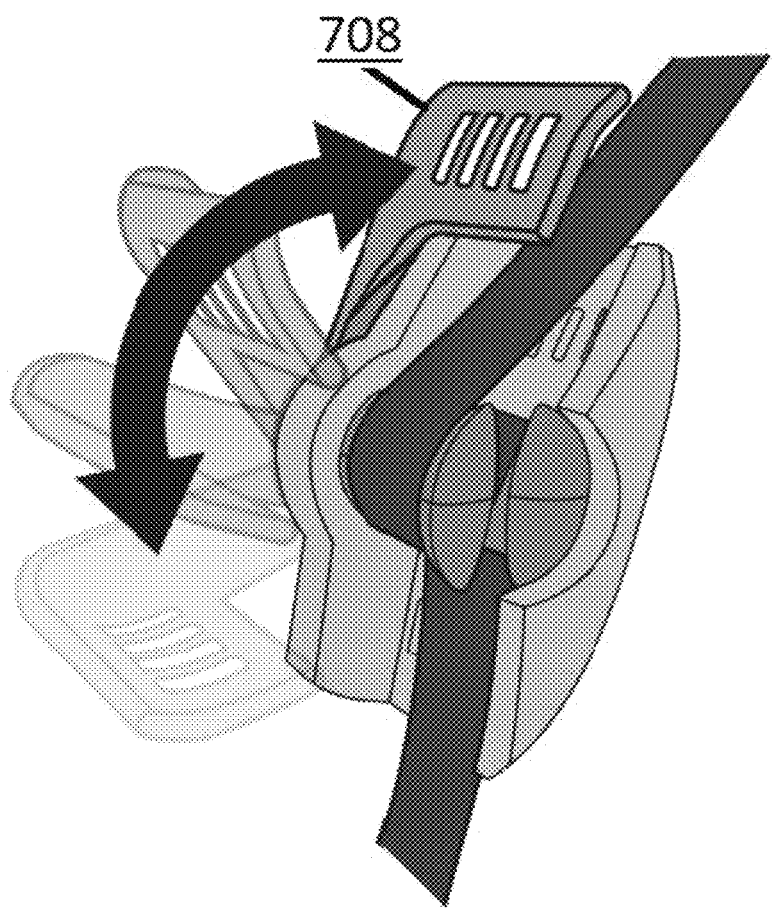
FIG. 11 illustrates the operation of the compression device.

Referring now to FIG. 11, illustrated is 1" wide webbing strap interacting with the compression device. The webbing is spooled around the central spooling mechanism as the ratchet handle is operated. The simple operation of the system can enable the system to be operated in high stress environment with low motor skills. The side loading of the spooling mechanism can enable a user to slide the side of the device onto a desired strap and then tighten the strap.

Still referring to FIG. 11, the ratchet handle also enables the device to be easily operated in a low motor skill situation as a push ratchet is an easier motion to accomplish in a low motor skill environment. The webbing strap is inserted using the side of the webbing strap rather than the end of the webbing strap. This can enable the device to be used in situations where the end of the strap cannot be found/there is no end to the strap. The system can be light weight. For example, the compression device can include lightweight materials, such as hard plastics.

Still referring to FIG. 11, the system can include a release to remove device more easily and this release can also be used to release pressure for allowing blood to flow to the injured limb. The nature of the compression device allows for gradual release of the tourniquet, enabling a more controlled flow of blood.

Figure 12:
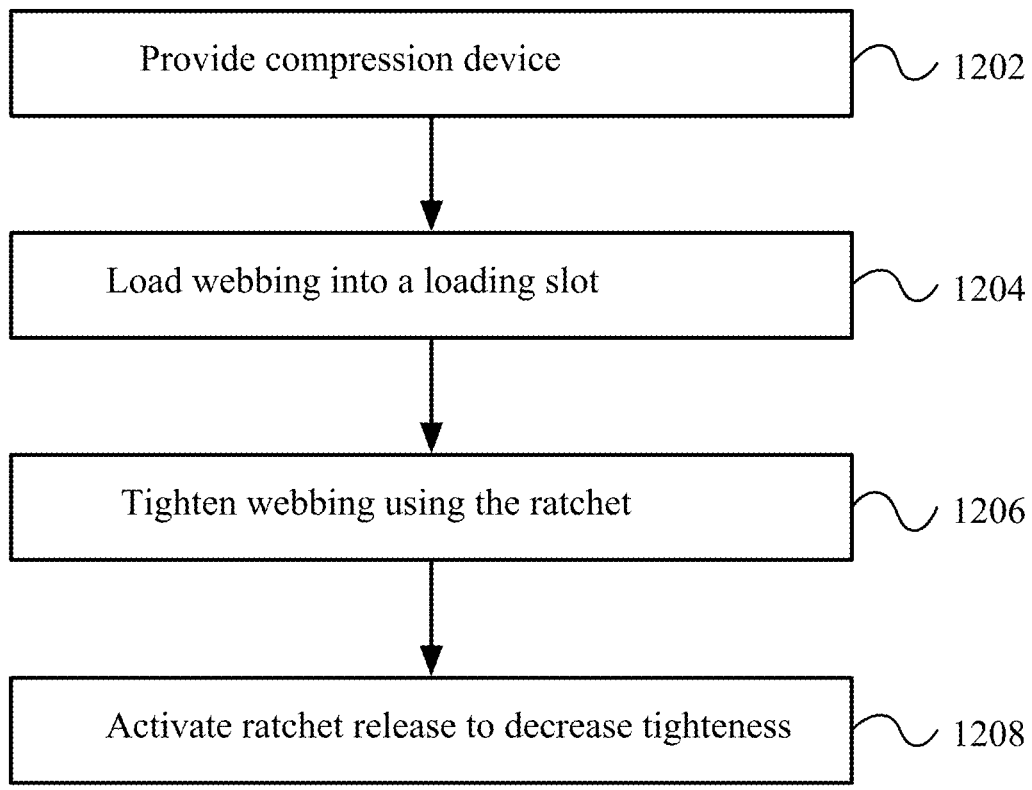
FIG. 12 illustrates a flow diagram of an example method for controlling a hemorrhage using the system illustrated in FIG. 1.

Referring now to FIG. 12, illustrated is a flow diagram of an example method 1200 for controlling a compression device described herein. The method 1200 includes providing a compression control device (step 1202). Loading a webbing into a side loading slot for spooling (step 1204). Tighten the webbing using the ratchet to apply a compressive and constrictive force to the wearer of the compression device (step 1206). A ratchet release system activates to relieve pressure (step 1208).

Still referring to FIG. 12, the example method 1200 includes providing a compression device (step 1202). The compression device can be any of the compression device devices described herein. With reference to FIGS. 1-11, the provided compression devices include compression device 106, compression device 106a, and compression device 106b. The provided compression device can include a profile surface 702 and a release system 704. The profiled surface generates a pressure profile designed to put force against the body and apply pressure to the area. The release system 704 can include button that can be pressed inwards to move the gear away from the pawl. The release system can enable a user to release tension in the webbing. The compression device 106 can function by two pawls operating against a ratchet gear. To operate the ratchet gear, the user lifts up and down on the handle. To release, the user presses the button which moves the gear away from the pawls, enabling the spooling mechanism to rotate freely. The provided compression device can include a safety release 706. The safety release 706 can prevent accidental release of the system. The provided compression device can include a ratchet handle 708. The ratchet handle 708 engages with and activates the internal ratcheting system. The provided compression device can include a spooling mechanism 710. The spooling mechanism 710 can include a barrel that twists the webbing. The compression device can include a surface 712 containing written or identifying information, such as the time that the tourniquet was applied. The provided compression device can include a side insertion slot 714 where the webbing is inserted into the barrel of the spooling mechanism. The side insertion slot 714 can be slanted as to provide easier sideways strap insertion. The compression device can include a ratchet handle, spooling component, a pawl ratchet tensioning device, a fixed end of webbing, and a fixed end fitting.

Still referring to FIG. 12, the method 1200 also includes loading a webbing into a side loading slot for spooling (step 1204). In some implementations, the webbing inserts into the slot 804 of the barrel 802. In some implementations, the webbing loads into slot 804a. In an alternate implementation, the webbing loads into slot 804a and slot 804b. In an alternate implementation, the webbing loads into slot 804a, slot 804b, and slot 804c. In an alternate implementation, the webbing loads into slot 804a, slot 804b, slot 804c, and slot 804d. In some implementations, the webbing strap is inserted using the side of the webbing strap rather than the end of the webbing strap. The compression device tightens the webbing around the junctional area. Inserting the webbing in the side loading ratchet can use lower motor skill when compared to traditional ratchets. The ratchet can be configured for side entry loading of the webbing. For example, rather than hand feeding the webbing through the central spooling component, a side of the ratchet can be exposed to enable the webbing to be directly inserted into the spooling component. In some implementations, the webbing strap meets with the spooling mechanism. In some implementations, the webbing stays against the body of the pressing device because of the metal bar 810. In some implementations, the webbing is loaded across the metal bar to add pressure and stability.

Still referring to FIG. 12, the method 1200 also includes tightening the webbing using the ratchet to apply a compressive and constrictive force to a fixed end arterial area of a body (step 1206). In some implementations, the force is applied to the wearer of the hemorrhage control device A ratchet handle 708 can lift up and down to activate the compression device. In some implementations, the ratchet handle 708 grips the webbing via slits 902a-902d. In some implementations, the ratchet handle 708 grips the webbing via slits 902a-902d when the ratchet handle 708 moves up and down to tighten the webbing. In some implementations, the profile surface slits 906a-906d grip the webbing. In some implementations, the profile surface slits 906a-906d grips the webbing when the ratchet handle 708 moves up and down to tighten the webbing.

The webbing is spooled around the central spooling mechanism as the ratchet handle 708 is operated. The activated 708 handle increases pressure by increasing the tension in the webbing. The ratchet handle 708 causes the spooling mechanism to gather webbing which in turn, tightens webbing strap and provides desired pressure. The compression device can constrict the webbing to provide a compressive force to the location. In some implementations, the location is an arterial location or the junctional area. The compression device applies pressure to a specific arterial location. The pressure is achieved by the constriction of the webbing strap and the form of the device pressing into the body. For example, the compression device can be coupled with the webbing over a specific arterial location to provide a compressive force to the arterial location as the compression device constricts the webbing. The side loading slot can work with webbings that are not open ended strap systems. For example, rather than inserting an open end of the webbing into the spooling component, both ends of the webbing can be coupled with a target and a length of the webbing between the ends can be slid into the side loading spool. In some implementations, the webbing is loaded into a second loading slot. In some implementations, a barrel twists the webbing. A handle can engage the internal ratcheting system. A safety release activates to prevent the ratchet gear from disengaging with the pawl. In some implementations, the safety release prevents the pawl from disengaging with the ratchet gear when the safety release is active. In some implementations, the safety release is a lever. In an alternate implementation, the safety release is a braking system.

Still referring to FIG. 12, the method 1200 also includes activating the ratchet release system to relieve pressure (step 1208). The release mechanism removes the ratchet to periodically allow blood to flow into the injured limb. This can result in less tissue loss and damage. The ratchet release system can activate by pressing a button. The button moves or disengages the ratchet gear from the pawl. In some implementations, the button moves or disengages the pawl from the ratchet gear. The ratchet release system activates when the safety release system is inactive. Activating the ratchet release system release the tension in the webbing. In some implementations, activating the ratchet release system enables blood flow to a limb of a subject. In some implementations, activating the ratchet release system removes the webbing from the first loading slot. In some implementations, activating the ratchet release system removes the webbing from the second loading slot. In some implementations, the release system 1004 moves the internal ratchet gear away from the pawls. In some implementations, the release system 1008 moves the pawl away from the gear. In some implementations, the release system 1002 operates via a lever. In some implementations, the release system 1008 operates via a button. In some implementations, the safety releases can prevent the release system 1004 and the release system 1008 from moving.

The disclosed system and methods may be embodied in other specific forms without departing from the spirit or essential characteristics thereof. The forgoing implementations are therefore to be considered in all respects illustrative, rather than limiting of the invention.

What is claimed is:

1. A tourniquet system comprising:
a compression device comprising:
  a spooling mechanism comprising:
    a barrel configured to rotate to twist at least one tourniquet strap at least partially around the barrel, the barrel comprising:
    a first side loading slot and a second side loading slot configured to receive a first tourniquet strap; and
    a third side loading slot and a fourth side loading slot configured to receive a second tourniquet strap;
  a ratchet release to disengage a ratchet gear from a pawl;
  a safety release to prevent the ratchet gear from disengaging with the pawl when the safety release is active; and
  a profile surface to generate a pressure against a subject.

2. The tourniquet system of claim 1, wherein the compression device further comprises a fixed end of webbing.

3. The tourniquet system of claim 2, wherein the spooling mechanism is configured to gather the webbing.

4. The tourniquet system of claim 3, wherein the compression device includes a preset pressure profile.

5. The tourniquet system of claim 1, wherein the compression device further comprises a fixed end fitting.

6. The tourniquet system of claim 1, wherein the compression device is configured for side entry loading of at least one of the first tourniquet strap or the second tourniquet strap, wherein the at least one of the first tourniquet strap of the second tourniquet strap is inserted into the compression device using a side of the first or second tourniquet strap rather than an end of the first or second tourniquet strap.

7. The tourniquet system of claim 1, wherein the first tourniquet strap and the second tourniquet strap are configured to press into the subject.

8. The tourniquet system of claim 1, further comprising a button to actuate the ratchet release.

9. The tourniquet system of claim 8, wherein the button moves the ratchet gear from the pawl.

10. A tourniquet system comprising:
a compression device comprising:
  a spooling mechanism having a barrel comprising a first side loading slot and a second side loading slot configured to receive a tourniquet strap;
  a ratchet release disengaging a pawl from a ratchet gear;
  a safety release to prevent the pawl from disengaging with the ratchet gear when the safety release is active; and
  a profile surface to generate a pressure profile against a subject.

11. The tourniquet system of claim 10, wherein rotation of the barrel pulls a first part of the tourniquet strap in a first direction and pulls a second part of the tourniquet strap in a second direction.

12. The tourniquet system of claim 10, wherein the tourniquet strap extends across the profile surface from a first end of the profile surface to a second end of the profile surface, and the barrel is disposed between the first end and the second end.

* * * * *